United States Patent [19]

Boroschewski et al.

[11] 4,315,769
[45] * Feb. 16, 1982

[54] HERBICIDALDIURETHANES AND THEIR USE

[75] Inventors: Gerhard Boroschewski; Friedrich Arndt, both of Berlin, Fed. Rep. of Germany

[73] Assignee: Schering AG, Berlin and Bergkamen, Fed. Rep. of Germany

[*] Notice: The portion of the term of this patent subsequent to Aug. 14, 1996, has been disclaimed.

[21] Appl. No.: 96,576

[22] Filed: Nov. 21, 1979

Related U.S. Application Data

[63] Continuation of Ser. No. 610,909, Sep. 5, 1975, abandoned, which is a continuation of Ser. No. 444,409, Feb. 21, 1974, abandoned.

[30] Foreign Application Priority Data

Mar. 1, 1973 [DE] Fed. Rep. of Germany ....... 2310649

[51] Int. Cl.$^3$ .............................................. A01N 37/44
[52] U.S. Cl. .......................................... 71/111; 71/98; 71/100
[58] Field of Search .......................................... 71/111

[56] References Cited

U.S. PATENT DOCUMENTS

| | | | |
|---|---|---|---|
| 3,404,975 | 10/1968 | Wilson et al. | 71/100 |
| 3,792,994 | 2/1974 | Baker et al. | 71/111 |
| 3,901,936 | 8/1975 | Boroschewski | 71/111 |
| 4,164,414 | 8/1979 | Arndt et al. | 71/111 |
| 4,229,208 | 10/1980 | Boroschewski et al. | 71/111 |

FOREIGN PATENT DOCUMENTS

| | | | |
|---|---|---|---|
| 1531794 | 7/1967 | France | 71/111 |
| 1536108 | 9/1967 | France | 71/111 |

OTHER PUBLICATIONS

Schering II, "N-alkyl-N-(carbarmoyloxyphenyl) carbamates", (1968) CA 71 No. 101513 v. (1969).

Primary Examiner—Glennon H. Hollrah
Attorney, Agent, or Firm—Michael J. Striker

[57] ABSTRACT

Diurethanes of the formula

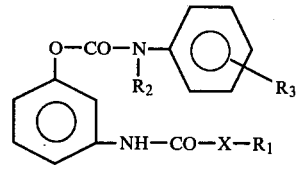

selectively damage or destroy weeds in crops of carrots, cotton, peanuts, and rice without damaging the crop plants when $R_1$ is methyl or ethyl; $R_2$ is propyl, butyl, isobutyl, or benzyl; $R_3$ is hydrogen, methyl, ethyl, methoxy, or methylmercapto; and X is oxygen or sulfur.

8 Claims, No Drawings

HERBICIDALDIURETHANES AND THEIR USE

This application is a continuation of Ser. No. 610,909, filed Sept. 5, 1975, now abandoned, which was a continuation of Ser. No. 444,409, filed Feb. 21, 1974, now abandoned.

The invention relates to selective herbicides and particularly to novel, herbicidal diurethanes and a method of using the same.

The known herbicides which are diurethanes are effective in controlling weeds in crops of sugar beets and other, economically less important crops, but they damage cotton plants severely when employed in amounts effective to destroy the weeds.

The object of this invention is the provision of herbicides which can be used to advantage in cotton crops to control weeds without damaging the crop plants.

It has been found that compounds of the formula

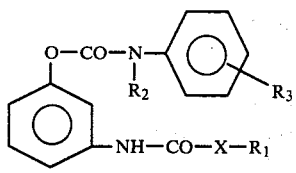

selectively control weeds in crops of cotton, but also in carrots, peanuts, and rice, without doing significant damage to the crop plants when $R_1$ is methyl or ethyl; $R_2$ is propyl, butyl, isobutyl, or benzyl; $R_3$ is hydrogen, methyl, ethyl, methoxy, or methylmercapto; and X is oxygen or sulfur.

The compounds of the invention differ from known, chemically related herbicides by being well tolerated by cotton plants in all stages of development, even by cotton seedlings. The compounds may thus be applied to weeds intermingled with the cotton plants at any stage of cultivation, and it is not necessary to postpone treatment until the cotton plants have matured, permitting a corresponding growth of weeds, as was necessary heretofore.

When the compounds of the invention are applied to cotton fields in the post-emergence stage of the cotton plants, they not only damage or destroy the weeds above ground but also act on germinating weed seeds which have not yet emerged.

The compounds of the invention are also effective in an analogous manner in crops of carrots, peanuts, and rice. They destroy or damage a wide variety of weeds including *Setaria verticillata, Amarantus spinosus, Datura stramonium, Portulaca oleracea, Xanthium pensylvanicum, Eleusine indica, Rottboellia exaltate,* Sinapis sp., Solanum sp., *Stellaria media, Snecio vulgaris, Lamium amplexicaule, Centaurea cyanus, Amarantus retroflexus, Galium aparine, Chrysanthemum segetum, Echinochloa crus galli, Setaria italica, Ipomoea purpurea, Polygonum lapathifolium, Digitaria sanguinalis,* and *Setaria faberi.*

The normal rate of application for selective effects on weeds is generally 0.5 kg to 5 kg of active compound per hectare, but application rates as high as 10 kg/ha may be employed if necessary without major crop damage.

Each compound of the invention may be employed as the sole active ingredient of a herbicidal composition, but the compounds may also be applied jointly with each other and with other herbicides and with addition agents not having herbicidal effects of their own. Surfactants synergistically enhance the selective herbicidal effects of the compounds of the invention in a manner known in itself.

The compounds are applied to weeds and crop plants in a conventional manner and are normally diluted with inert carriers for ease of handling. The compositions so obtained may be pulverulent or granular solids or liquids in which the compounds of the invention are dissolved in organic solvents or dispersed as a separate phase in a liquid carrier in which they are not adequately soluble. Calcium lignosulfonate, polyoxyethyleneoctylphenol ethers, naphthalenesulfonic acids, phenolsulfonic acids, formaldehyde condensation products, fatty alcohol sulfates, and the alkali and alkaline earth salts of fatty acids may be employed to enhance the wetting of the weeds by liquid compositions and to improve the selective herbicidal effect, particularly when the surfactants are employed in amounts greater than those needed for producing a maximum reduction of surface tension.

The active agents of the invention are most conveniently applied in the form of compositions in which they are mixed with inert, liquid or solid carriers in ratios of 4:1 to 1:4, and the mixtures may contain up to 30% surfactant.

The mode of application may be chosen to suit conditions as is well known. Aqueous compositions containing the necessary amount of at least one active agent of the invention may be sprayed on the weed-infested crops in amounts of 100 liter/ha to 1000 liter/ha, these application rates being merely typical and not critical.

The compounds of the invention are prepared by known reactions as by reacting compounds of the formulas

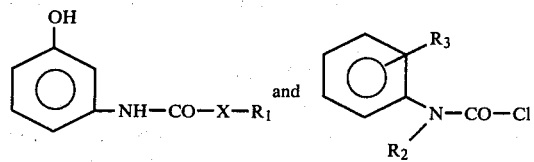

with each other in the presence of triethylamine or pyridine at 0° to 100° C.

They may also be prepared by reacting an amine of the formula

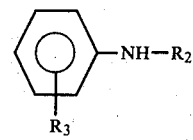

with a compound of the formula

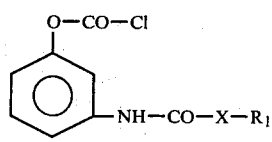

in the presence of an acid acceptor.

Another synthesis starts from compounds of the formula

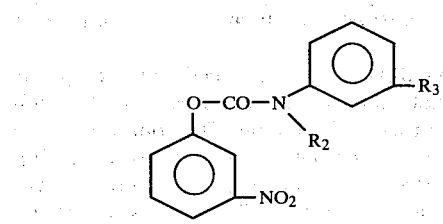

which are hydrogenated in methanol solution in the presence of a Raney nickel catalyst, and the amines so obtained are reacted with compounds of the formula $R_1$—X—CO—Cl, in all the above formulas, $R_1$, $R_2$, $R_3$, and X being as defined initially.

The following Examples illustrate the methods of producing and using the compounds of this invention.

EXAMPLE 1

A solution of 22.9 g chloroformic acid 3-(N-carbomethoxyamino)-phenyl ester in 50 ml ethyl acetate and a solution of 13.8 potassium carbonate in 50 ml water were added simultaneously and dropwise to a mixture of 14.9 g isobutylaniline, 50 ml water, and 30 ml ethyl acetate at 10° to 15° C. with stirring. After the mixing of all ingredients, stirring was continued while the mixture was cooled with ice. The organic phase then was separated from the aqueous phase of the mixture, washed at 0° C. with a little dilute sodium hydroxide solution and with water, dried with magnesium sulfate, and partly evaporated in a vaccum. The residue was mixed with pentane, whereby methyl N-3-(N-isobutyl-N-phenylcarbamoyloxy)-phenyl-carbamate was crystallized in an amount of 23.3 g (68% yield). It melted at 128° to 129° C.

The compound will be referred to hereinafter as Compound No. 1.

EXAMPLE 2

16.7 g 3-Hydroxycarbanilic acid methyl ester was converted to the sodium salt by reaction with sodium methylate (containing 2.3 g Na) in anhydrous methanol. The solvent was removed in a vacuum, and the sodium salt was suspended in 100 ml dry methylisobutylketone. A solution of 21.2 g N-isobutyl-N-phenylcarbamoyl chloride in 50 ml dry methylisobutylketone was added dropwise at 70° C. with stirring, and stirring was continued at the same temperature for 45 minutes.

The reaction mixture then was cooled to 0° C., washed at this temperature with a little dilute sodium hydroxide solution and with water, dried with magnesium sulfate, and evaporated to dryness in a vacuum. The residue was mixed with ethyl ether, whereby crystallization of ethyl N-3-(N-isobutyl-N-phenylcarbamoyloxy)-phenyl-carbamate (Compound No. 2) was induced. The yield was 23.1 g (65%), the melting point of the compound 100° to 101° C.

The compounds listed in Table I were prepared in an analogous manner. They are readily soluble in acetone, cyclohexanone, ethyl acetate, isophorane, ethyl ether, and tetrahydrofurane, but practically insoluble in water and a petroleum fraction boiling at 60° to 110° C.

Among the compounds listed, Compounds Nos. 1, 2, 3, 4, 7, 9, 10, 11, 12, and 13 are particularly effective as selective herbicides in crops of cotton, carrots, peanuts, and rice.

EXAMPLE 3

The plants listed in Table II were sprayed in a greenhouse in the post-emergence stage with the compounds of the invention indicated in the Table at a rate of 3 kg/ha of active agent dispersed in 500 liters water per hectare. The plants were at an early stage of development. They were inspected 14 days after the spraying, and the results observed were evaluated on an empirical, but reproducible scale on which a value of zero indicates total destruction, and a value of 10 the absence of damage. These values are listed in Table II.

The plants are identified in all Tables by capital letters as follows:
CO Cotton
PE Peanut
PL *Polygonum lapathiofolium*
SM *Stellaria media*
SV *Senecio vulgaris*
LA *Lamium amplexicaule*
CC *Centaurea cyanus*
AR *Amarantus retroflexus*
CS *Chrysanthemum segetum*
IP *Ipomoea purpurea*
EC *Echinochloa crus galli*
SI *Setaria italica*
DS *Digitaria sanguinalis*
SF *Setaria faberi*
AS *Amarantus spinosum*
XP *Xanthium pensylvanicum*
PO *Portulaca oleracea*
SE *Setaria verticillata*
RE *Rottboellia exaltata*
EI *Eleusine indica*

While not specifically included in Table II, carrots and rice were equally unaffected by the compounds of the invention. Closely corresponding results were achieved with the analogs of the listed compounds in which $R_3$ was $CH_3$—S—, methylmercapto, specific reference being had to the analogs of Compounds Nos. 20, 21, 24, 31, 33, 36, and 37.

For comparison purposes, control tests were simultaneously run under the same conditions with the known herbicide N-3-trifluoromethylphenyl-N,N-dimethylurea. It destroyed most of the tested weeds, but also completely destroyed the cotton plants, and also completely destroyed the peanut plants. In another series of control tests, methyl N-3-(N-3-methylphenylcarbamoyloxy)phenyl-carbamate showed variable results on the tested weeds, destroying or almost destroying some, but also the peanut plants, and doing as much serious damage to cotton as to some other weeds. *Polygonum lapathifolium* was most resistant to the last-mentioned herbicide among all the tested plants, and substantially more resistant than cotton.

EXAMPLE 4

Weed plants in an early stage of development were sprayed in a greenhouse test with Compounds Nos. 3 and 4 at a rate of 2 kg active agent emulsified in 500 liters water per hectare. The plants were inspected 14 days after the treatment, and the results were evaluated as in the preceding Example. The results are shown in Table III.

TABLE I

| Comp'd No. | | M.P., °C. or $n_D^{20}$ |
|---|---|---|
| 3 | Methyl N-3-(N-n-butyl-N-phenyl-carbamoyloxy)-phenyl-carbamate | 82–85 |
| 4 | Ethyl N-3-(N-n-butyl-N-phenyl-carbamoyloxy)-phenyl-carbamate | 1.5349 |
| 5 | Methyl N-3-(N-isobutyl-N-3-methylphenyl-carbamoyloxy)-phenyl-carbamate | 76–80 |
| 6 | Ethyl N-3-(N-isobutyl-N-3-methylphenyl-carbamoyloxy)-phenyl-carbamate | 79–80 |
| 7 | S-Methyl N-3-(N-isobutyl-N-3-methylphenyl-carbamoyloxy))-phenyl-thiocarbamate | 119–121 |
| 8 | Methyl N-3-(N-phenyl-N-benzyl-carbamoyloxy)-phenyl-carbamate | 83–86 |
| 9 | S-Methyl N-3-(N-isobutyl-N-phenyl-carbamoyloxy)-phenyl-thiocarbamate | 96–98 |
| 10 | S-Methyl N-3-(N-n-butyl-N-phenyl-carbamoyloxy)-phenyl-thiocarbamate | 83–85 |
| 11 | Methyl N-3-(N-propyl-N-phenyl-carbamoyloxy)-phenyl-carbamate | 97–98 |
| 12 | Ethyl N-3-(N-propyl-N-phenyl-carbamoyloxy)-phenyl-carbamate | 105–106 |
| 13 | S-Methyl N-3-(N-propyl-N-phenyl-carbamoyloxy)-phenyl-thiocarbamate | 94–96 |
| 14 | Methyl N-3-(N-n-butyl-N-4-ethylphenyl-carbamoyloxy)-phenyl-carbamate | 73–76 |
| 15 | S-Methyl N-3-(N-benzyl-N-phenyl-carbamoyloxy)-phenyl-thiocarbamate | 129–131 |
| 16 | Ethyl N-3-(N-benzyl-N-phenyl-carbamoyloxy)-phenyl-carbamate | 83–85 |
| 17 | S-Ethyl N-3-(N-butyl-N-phenyl-carbamoyloxy)-phenyl-thiocarbamate | 85–87 |
| 18 | S-Methyl N-3-(N-2-methylphenyl-N-propyl-carbamoyloxy)-phenyl-thiocarbamate | 120–123 |
| 19 | S-Methyl N-3-(N-3-methylphenyl-N-propyl-carbamoyloxy)-phenyl-thiocarbamate | 103–104 |
| 20 | Methyl N-3-(N-3-methoxyphenyl-N-propyl-carbamoyloxy)-phenyl-carbamate | 87–88 |
| 21 | Methyl N-3-(N-butyl-N-3-methoxyphenyl-carbamoyloxy)-phenyl-carbamate | 74–75 |
| 22 | S-Methyl N-3-(N-4-methylphenyl-N-propyl-carbamoyloxy)-phenyl-thiocarbamate | 101–102 |
| 23 | S-Methyl N-3-N-4-ethylphenyl-n-propylcarbamoyloxy)-phenyl-thiocarbamate | 96–97 |
| 24 | S-Methyl N-3-(N-3-methoxyphenyl-N-propylcarbamoyloxy)-phenyl-thiocarbamate | 103–105 |
| 25 | Methyl N-3-(N-4-ethylphenyl-N-propylcarbamoyloxy)-phenyl-carbamate | 1.5487 |
| 26 | S-Methyl N-3-(N-butyl-N-3-methoxyphenyl-carbamoyloxy)-phenyl-thiocarbamate | 106–107 |
| 27 | Ethyl N-3-(N-2-methylphenyl-N-propylcarbamoyloxy)-phenyl-carbamate | 1.5472 |
| 28 | Ethyl N-3-(N-3-methylphenyl-N-propylcarbamoyloxy)-phenyl-carbamate | 85–87 |
| 29 | Ethyl N-3-(N-4-ethylphenyl-N-propylcarbamoyloxy)-phenyl-carbamate | 1.5436 |
| 30 | Ethyl N-3-(N-4-methylphenyl-N-propylcarbamoyloxy)-phenyl-carbamate | 88–89 |
| 31 | Ethyl N-3-(N-3-methoxyphenyl-N-propylcarbamoyloxy)-phenyl-carbamate | 93–94 |
| 32 | S-Ethyl N-3-(N-3-methylphenyl-N-propylcarbamoxloxy)-phenyl-thiocarbamate | 84–86 |
| 33 | Ethyl N-3-(N-butyl-N-3-methoxyphenyl-carbamoyloxy)-phenyl-carbamate | 72–73 |
| 34 | S-Ethyl N-3-(N-2-methylphenyl-N-propylcarbamoyloxy)-phenyl-thiocarbamate | 111–113 |
| 35 | S-Ethyl N-3-(N-4-methylphenyl-N-propylcarbamoyloxy)-phenyl-thiocarbamate | 1.5617 |
| 36 | S-Ethyl N-3-(N-3-methoxyphenyl-N-propylcarbamoyloxy)-phenyl-thiocarbamate | 88–89 |
| 37 | S-Ethyl N-3-(N-butyl-N-3-methoxyphenyl-carbamoyloxy)-phenyl-thiocarbamate | 66–68 |
| 38 | Methyl N-3-(N-2-methylphenyl-N-propylcarbamoyloxy)-phenyl-carbamate | |
| 39 | Methyl N-3-(N-3-methylphenyl-N-propylcarbamoyloxy)-phenyl-carbamate | |
| 40 | Methyl N-4-(N-4-methylphenyl-N-propylcarbamoyloxy)-phenyl-carbamate | |

TABLE II

| Comp'd No. | CO | PE | PL | SM | SV | LA | CC | AR | CS | IP | EC | SI | DS | SF |
|---|---|---|---|---|---|---|---|---|---|---|---|---|---|---|
| 3 | 10 | 10 | 0 | 0 | 0 | 0 | 0 | 0 | 0 | 0 | 0 | 0 | 0 | 0 |
| 4 | 10 | 10 | 0 | 0 | 0 | 0 | 0 | 0 | 0 | 0 | 0 | 0 | 0 | 0 |
| 1 | 10 | 10 | 0 | 0 | 0 | 0 | 0 | 0 | 0 | 0 | 0 | 0 | 0 | 0 |
| 5 | 10 | — | 0 | 0 | 0 | 0 | 0 | 0 | 0 | 0 | 0 | 0 | 0 | 0 |
| 6 | 10 | 10 | 0 | 0 | 0 | 0 | 0 | 0 | 0 | 0 | 0 | 0 | 0 | 0 |
| 7 | 10 | 10 | 0 | 0 | 0 | 0 | 0 | 0 | 0 | 0 | 0 | 0 | 0 | 0 |
| 8 | 10 | 10 | 0 | 0 | — | 0 | 1 | 0 | 0 | 0 | 0 | 0 | — | 0 |
| 2 | 10 | 10 | 0 | 1 | 0 | 0 | 0 | 0 | 0 | 0 | 0 | 0 | 0 | 0 |
| 9 | 10 | 10 | 0 | 0 | 0 | 0 | — | 0 | 0 | 0 | 0 | 0 | — | 0 |
| 10 | 10 | 10 | 0 | 0 | 0 | 0 | — | 0 | 0 | 0 | 1 | 0 | — | 0 |
| 11 | 10 | 10 | 0 | 0 | 0 | 0 | 0 | 0 | 0 | 0 | 0 | 0 | 0 | 0 |
| 12 | 10 | 10 | 0 | 0 | 0 | 0 | 0 | 0 | 0 | 0 | 0 | 0 | 0 | 0 |
| 13 | — | 10 | 0 | 0 | 0 | 0 | 0 | 0 | 0 | 0 | 0 | 0 | 0 | 0 |
| 18 | — | 9 | 0 | 0 | 0 | 0 | 0 | 0 | 0 | — | 0 | 0 | 0 | 0 |
| 19 | — | 9 | 0 | 0 | 0 | 0 | 0 | 0 | 0 | 0 | 2 | 0 | 0 | 0 |
| 20 | 8 | 10 | 0 | 5 | 4 | 0 | 0 | 1 | 0 | 0 | 2 | 0 | 0 | 0 |
| 21 | 9 | 10 | 0 | 4 | 7 | 0 | 0 | 0 | 0 | 0 | 3 | 0 | 0 | 0 |
| 22 | — | 10 | 0 | 0 | 0 | 0 | 0 | 0 | 0 | 0 | 2 | 0 | 0 | 0 |
| 23 | — | 9 | 0 | 0 | 0 | 0 | 0 | 0 | 0 | 0 | 4 | 0 | 0 | 1 |
| 24 | — | 10 | 0 | 0 | 0 | 0 | 0 | 0 | 0 | 0 | 1 | 0 | 0 | 1 |
| 25 | — | 10 | 0 | 0 | 0 | 0 | 0 | 0 | 0 | 0 | 6 | 0 | 0 | 0 |
| 26 | — | 10 | 0 | 0 | 0 | 0 | 0 | 0 | 0 | 0 | 6 | 0 | 0 | 0 |
| 27 | 10 | 10 | 0 | 0 | 0 | 0 | 0 | 1 | 0 | 0 | 6 | 0 | 0 | 0 |
| 28 | 10 | 10 | 0 | 0 | 0 | 0 | 0 | 0 | 0 | 0 | 4 | 0 | 0 | 0 |
| 29 | — | 10 | 0 | 0 | 1 | 0 | 0 | 0 | 0 | 0 | 5 | 0 | 0 | 0 |
| 30 | — | 10 | 0 | 0 | 0 | 0 | 0 | 0 | 0 | 0 | 4 | 0 | 0 | 0 |
| 31 | 10 | 10 | 0 | — | — | 1 | 0 | 4 | 1 | 0 | 6 | 0 | 0 | 0 |
| 32 | 9 | 10 | 0 | 0 | — | 0 | 0 | 0 | 0 | 0 | 0 | 0 | 0 | 0 |
| 33 | 9 | 9 | 0 | — | 0 | 3 | 0 | 2 | 1 | 1 | 2 | 2 | 0 | — |
| 34 | 9 | 10 | 1 | 1 | 0 | 0 | 0 | 0 | — | 1 | 2 | 1 | 1 | — |
| 35 | 9 | 10 | 0 | 0 | 3 | 0 | 0 | 0 | 0 | 0 | 0 | 0 | 0 | 1 |
| 36 | 10 | 10 | 0 | 4 | 5 | 0 | 0 | 0 | 0 | 0 | 0 | 0 | 0 | 1 |
| 37 | 10 | 10 | 0 | 7 | 7 | 2 | 0 | 0 | 0 | 1 | 0 | 0 | 0 | 2 |
| 38 | — | 10 | 0 | 0 | 1 | 0 | 0 | 0 | 0 | 0 | 1 | 0 | 0 | 0 |
| 39 | — | 10 | 0 | 0 | 0 | 0 | 0 | 0 | 0 | 0 | 2 | 0 | 0 | 0 |

TABLE II-continued

| Comp'd No. | CO | PE | PL | SM | SV | LA | CC | AR | CS | IP | EC | SI | DS | SF |
|---|---|---|---|---|---|---|---|---|---|---|---|---|---|---|
| 40 | — | 8 | 0 | 0 | 0 | 0 | 0 | 0 | 0 | 0 | 4 | 0 | 0 | 4 |
| 14 | 10 | 10 | 0 | 0 | — | 1 | 0 | 0 | 0 | 0 | 0 | 0 | 0 | 0 |
| 15 | 10 | 10 | 0 | 0 | 0 | 0 | 0 | 0 | 0 | 0 | 0 | 0 | 0 | 1 |
| 16 | 10 | 10 | 0 | 1 | — | 0 | 2 | 0 | 2 | — | 3 | 1 | 0 | 0 |

TABLE III

| Compound No. | AS | XP | PO | SE | RE | SI |
|---|---|---|---|---|---|---|
| 3 | 0 | 0 | 0 | 0 | 1 | 2 |
| 4 | 0 | 0 | 0 | 0 | — | — |

What is claimed is:

1. A method of controlling weeds in a crop of cotton, comprising the step of applying to said weeds and to said crop an effective amount of a herbicidal compound of the formula

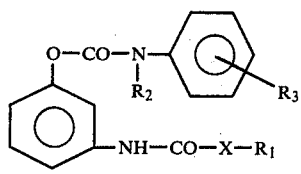

wherein
$R_1$ is methyl or ethyl;
$R_2$ is propyl, butyl, isobutyl, or benzyl;
$R_3$ is hydrogen, methyl, ethyl, or methoxy and
X is oxygen.

2. A method as set forth in claim 1, wherein said compound is applied to said weeds and to said crop in the post-emergence stage.

3. A method as set forth in claim 1, wherein said effective amount comprises 1 to 3 kg of active compound per hectare.

4. A method as set forth in claim 1, further comprising, before application, the step of adding to said compound inert liquid or solid carriers.

5. The method of claim 4, wherein the ratio of said compound to said carriers is between 4:1 and 1:4.

6. A method as set forth in claim 1, further comprising, before application, the step of adding surfactants to said compound.

7. The method of claim 6, wherein said surfactants are added in an amount up to about 30% of the total weight.

8. The method of claim 1, wherein said herbicidal compound is ethyl-N-[3-(N-propyl-N-phenylcarbamoyloxy)-phenyl]-carbamate.

* * * * *